United States Patent [19]

Gorfine

[11] Patent Number: 5,693,676
[45] Date of Patent: Dec. 2, 1997

[54] NITRIC OXIDE DONOR COMPOSITION AND METHOD FOR TREATMENT OF ANAL DISORDERS

[75] Inventor: Stephen R. Gorfine, New York, N.Y.

[73] Assignee: Neptune Pharmaceutical Corporation, Kansas City, Mo.

[21] Appl. No.: 666,264

[22] Filed: Jun. 20, 1996

Related U.S. Application Data

[63] Continuation of Ser. No. 371,088, Jan. 10, 1995, abandoned, which is a continuation-in-part of Ser. No. 250,555, May 27, 1994, Pat. No. 5,504,117.

[51] Int. Cl.$^6$ ............................................. A61K 31/04
[52] U.S. Cl. ........................... 514/742; 514/470; 514/740; 514/171; 514/179; 514/312; 514/882; 514/929
[58] Field of Search ............................. 514/742, 179, 514/535, 882, 929, 740, 171, 312

[56] References Cited

U.S. PATENT DOCUMENTS

| | | | |
|---|---|---|---|
| 814,408 | 3/1906 | Steele | 604/289 |
| 2,840,080 | 6/1958 | Clark | 604/289 |
| 4,118,480 | 10/1978 | Williams | 424/653 |
| 4,292,299 | 9/1981 | Suzuki et al. | 424/435 |
| 5,059,603 | 10/1991 | Rubin | 514/264 |
| 5,183,663 | 2/1993 | Greiner | 424/443 |

OTHER PUBLICATIONS

Rattan, et al., "Nitric Oxide Pathway in Rectoanal Inhibitory Reflex of Opossum Internal Anal Sphincter", *No As a Gut Smooth Muscle–Inhibitory Mediator,* 1992.
Rattan, et al., "Role of Nitric Oxide as a Mediatory of Internal Anal Sphincter Relaxation", *Nitric Oxide As Gut Smooth Muscle Inhibitory Mediator,* pp. G107–G112, 1991.
O'Kelly, et al., "Nerve Mediatd Relaxation of the Human Internal Anal Sphincter: The Role of Nitric Oxide", *Gut,* pp. 689–693, 1993.
Chakder, et al., "Release of Nitric Oxide by Activation of Nonadrenergic Noncholinergic Neurons of Internal Anal Sphincter", *No Release By Nanc Neural Stimulation and VIP,* pp. G7–G12, 1992.

Loder, et al., "Reversible Chemical Sphincterotomy by Local Application of Glyceryl Trinitrate", *British Journal of Surgery,* pp. 1386–1389, 1994.
Shafik, "Role of warm–water bath in anorectal; conditions: The 'thermosphincteric reflex.'" *J. Clin. Gastroenterol.,* 16:304–308, 1993.
Gillespie et al., "Influence of haemoglobin and erythrocytes on the effects of EDRF, a smooth muscle inhibitory factor, and nitric oxide on vascular and non–vascular smooth muscle,"*Br. J. Pharmacol.,* 95:1151–1156, 1988.
Ignarro et al., "Nitric oxide and cyclic GMP formation upon electrical field stimulation cause relaxation of corpus cavernosum smooth muscle,"*Biochem. Biophys. Res. Commun.,* 170:843–850, 1990.
Bult et al., "Nitric oxide as an inhibitory non–adrenergic non–cholinergic neurotransmitter,"*Nature,* 345:346–347, 1990.
Feelisch et al., "Correlation between nitric oxide formation during degradation of organic nitrates and activation of guanylate cyclase,"*Eur. J. Pharmacol.,* 139:19–30, 1987.
Fung et al., "Biochemical mechanism of organic nitrate action," *Am. J. Cardiol.,* 70:4B–10B, 1992.
Huff et al., (Eds.), "Physicians' Desk Reference," 41st Edition, Medical Economics Company, Oradell, N.J., 1987, at pp. 780, 1176–1178, 1533 and 1984–85.
Loder et al. "AGA Abstracts" *Gastroenterology,* vol. 104 No. 4, 1993.
Budavari et al. (Eds.), " The Merck Index,"11th Edition, Merck & Co., Rahway, N.J., 1989, pp. 198 and 821 (isopropyl nitrate).
Guillemot, et al., "Action of In Situ Nitroglycerin on Upper Anal Canal Pressure of Patients with Terminal Constipation" *Dis Colon Rectum,* Apr. 1993.

*Primary Examiner*—John W. Rollins
*Attorney, Agent, or Firm*—Shook, Hardy & Bacon L.L.P.

[57] ABSTRACT

A pharmaceutical composition contains a nitric oxide donor and advantageously an optional corticosteroid and/or topical anesthetic. The composition is useful in a method for treating anal disorders such as anal fissure, anal ulcer, hemorrhoidal disease, levator spasm, and so forth, by topical application to or proximate the affected area.

62 Claims, No Drawings

NITRIC OXIDE DONOR COMPOSITION AND METHOD FOR TREATMENT OF ANAL DISORDERS

This is a continuation of application Ser. No. 08/371,088 filed on Jan. 10, 1995 abandoned, which is a continuation-in-part of U.S. Ser. No. 08/250,555 filed Aug. 27, 1994, now U.S. Pat. No. 5,504,117, issued Apr. 2, 1996.

BACKGROUND OF THE INVENTION

This invention is directed to a composition and method for treating anal disorders such as anal fissure, anal ulcer, hemorrhoidal disease and levator spasm, by topical application of the composition to or proximate the affected area.

In general, anal fissure (fissure-in-ano), anal ulcer, acute hemorrhoidal disease, and levator spasm (proctalgia fugax) are common, benign conditions of the anal canal which affect humans of all ages, races and sexes. However, these conditions can be problematical to treat and inconvenient if not painful to endure. An anal fissure or ulcer is a tear or ulcer of the mucosa or lining tissue of the distal anal canal. Anal fissure/ulcer can be associated with other systemic or local diseases but is more frequently present as an isolated finding. The typical, idiopathic fissure or ulcer is confined to the anal mucosa, and usually lies in the posterior midline, distal to the dentate line. The person with an anal fissure or ulcer frequently experiences anal pain and bleeding, the pain being more pronounced during and after bowel movements.

Hemorrhoids are specialized vascular areas lying subjacent the anal mucosa. Symptomatic hemorrhoidal disease is manifest by bleeding, thrombosis and/or prolapse of the hemorrhoidal tissues. Commonly, internal hemorrhoidal tissue bulges into the anal canal during defecation causing bleeding and pain. As the tissue enlarges, further bleeding and pain, prolapse and thrombosis can ensue. The thrombosis of hemorrhoids is another cause of bleeding and pain.

Levator spasm is a condition affecting women more frequently than men. This syndrome is characterized by spasticity of the levator ani muscle, a portion of the anal sphincter complex. The patient suffering from levator spasm may experience severe, episodic rectal pain. Physical exam may reveal spasm of the puborectalis muscle and pain may be reproduced by direct pressure on this muscle. Bleeding is normally not associated with this condition.

The underlying causes of these anal disorders are poorly understood, but all of these conditions are associated with a relative or absolute degree of anal sphincter hypertonicity. In the case of anal fissure/ulcer, the abnormality appears to be an as-yet-unidentified problem of the internal anal sphincter muscle. The internal sphincter is a specialized, involuntary muscle arising from the inner circular muscular layer of the rectum. Intra-anal pressure measurements obtained from people suffering from typical anal fissure/ulcer disease show an exaggerated pressure response to a variety of stimuli. The abnormally high intra-anal pressure is generated by the internal sphincter muscle and is responsible for non-healing of the fissure or ulcer and the associated pain.

An abnormal pressure response in the anal canal has also been observed in people suffering from symptomatic hemorrhoidal disease. Elevated intra-anal pressures may be a major factor in the development of this condition. It has been postulated that the pain associated with acute hemorrhoidal disease is caused in part by spasm of the internal anal sphincter muscle. Similarly, the pain associated with levator spasm is induced by the muscle spasm itself.

Various therapies have been devised to treat these anal disorders. Typical, non-surgical therapy includes bulk laxatives and sitz baths. Sitz baths are helpful because they induce relaxation of the anal sphincter mechanism. See e.g., Shafik, "Role of warm-water bath in anorectal conditions: The 'thermosphincteric reflex,'" *J. Clin. Gastroenterol.*, 16:304–308, 1993.

Topical anal therapy is also used in an effort to promote healing, relieve pain, and reduce swelling and inflammation. Many preparations have been tried including those containing local anesthetics, corticosteroids, astringents, and other agents. However, none of these preparations has been shown conclusively to reduce the healing time or to reliably ameliorate associated pain.

In certain instances, surgery may be employed to treat anal disorders. Cases of anal fissure/ulcer or hemorrhoids recalcitrant to medical therapy are often referred for surgical treatment. In keeping with the proposed etiology of anal fissure/ulcer, the current standard surgical procedure therefor is lateral internal anal sphincterotomy. In this procedure, the internal anal sphincter muscle is partially cut, thereby reducing the intra-anal pressure. The lowered pressure allows the fissure/ulcer to heal and also relieves the associated pain. Surgical hemorrhoidectomy removes the redundant hemorrhoidal tissue, and many surgeons will perform concomitant limited internal anal sphincterotomy to lower anal canal pressure. There is no successful surgical treatment for levator spasm.

Recently, a third component of the autonomic nervous system, known as the enteric nervous system (ENS), has been described and elucidated. This neural network innervates the gut continuously from esophagus to anus. It is composed of enteric neurons, and the processes of extrinsic efferent and afferent neurons of the traditional autonomic system. This system regulates the motor and secretory function of the gut. A notable feature of the ENS is the diversity of chemical messengers which enteric neurons contain and release. In addition to acetylcholine and norepinephrine, various peptide and non-peptide substances have been identified which appear to function as neurotransmitters in the ENS. Inhibitory non-adrenergic non-cholinergic (NANC) nerves are thought to be important therein.

More recently, nitric oxide (NO) has been identified as an inhibitory transmitter to muscle. It has been shown that NO mediates the anorectal inhibitory reflex in animals and man. See e.g., Rattan et al., "Nitric oxide pathway in rectoanal inhibitory reflex of opossum internal anal sphincter," *Gastroenterology*, 103:43–50, 1992; Chakder et al., "Release of nitric oxide by activation of nonadrenergic noncholinergic neurons of internal anal sphincter," *Am. J. Physiol.*, 264:G7–G12, 1993; O'Kelley et al., "Nerve mediated relaxation of the internal anal sphincter: The role of nitric oxide," *Gut*, 34:689–693, 1993. See also, Gillespie et al., "Influence of haemoglobin and erythrocytes on the effects of EDRF, a smooth muscle inhibitory factor, and nitric oxide on vascular and non-vascular smooth muscle," *Br. J. Pharmacol.*, 95:1151–1156, 1988; Ignarro et al., "Nitric oxide and cyclic GMP formation upon electrical field stimulation cause relaxation of corpus cavernosum smooth muscle," Biochem. *Biophys. Res. Commun.*, 170:843–850, 1990; Bult et al., "Nitric oxide as an inhibitory non-adrenergic non-cholinergic neurotransmitter," *Nature*, 345:346–347 1990. It has been proposed that NO formation, based upon non-enzymatic NO release from various organic nitrates as catalyzed in the presence of cysteine, causes direct or indirect activation of the soluble guanylate cyclase, finally resulting in relaxation of vascular smooth muscle in vivo. See, Feelisch et al., "Correlation between nitric oxide formation during degradation of organic nitrates and activation of guanylate cyclase," *Eur. J. Pharmacol.*, 139:19–30, 1987. See also Fung et al., "Biochemical mechanism of organic nitrate action," *Am. J. Cardiol.*, 70:4B–10B, 1992.

Organic nitrates such as nitroglycerin (GTN), isosorbide dinitrate (ISDN), isosorbide mononitrate (ISMN), erythrityl tetranitrate (ETN), pentaerythrityl tetranitrate (PETN) are known to cause vasodilation and have been used for decades in the treatment of angina pectoris. See e.g., Huff et al. (Eds.), "Physicians' Desk Reference," 41st Edition, Medical Economics Company, Oradell, N.J., 1987, at pages 780, 1176–78, 1533 and 1984–85; Rubin, U.S. Pat. No. 5,059, 603 (October 1991); Budavari et al. (Eds.), "The Merck Index," 11th Edition, Merck & Co., Rahway, N.J., 1989, p. 821 (isopropyl nitrate); Fung et al., "Biochemical mechanism of organic nitrate action," *Am. J. Cardiol.*, 70:4B–10B, 1992.

Corticosteroids such as hydrocortisone have been used for the treatment of various benign anal disorders for many years. Studies of this treatment have shown some benefit thereby, but not in a reproducible nor significant fashion.

Topical anesthetics such as dibucaine, lidocaine, pramoxine, and others have been used for treatment of anal pain. However, any relief has been relatively short-lived.

Various other preparations are known. See e.g., Suzuki et al., U.S. Pat. No. 4,292,299 (September 1981), note column 5 lines 18–20 & 26–28; Rubin '603, note column 7, lines 61–65 & example 1; Greiner, U.S. Pat. No. 5,183,663 (February 1993). See also, Williams, U.S. Pat. No. 4,118, 480 (October 1978); Huff et al. (Eds.), "The Merck Index," 11th Edition, page 198.

SUMMARY OF THE INVENTION

It is an object of the present invention to provide an effective treatment for anal diseases such as anal fissure, anal ulcer, hemorrhoidal disease, and levator spasm, which treatment includes the rapid relief of pain associated with such diseases.

It is another object of the invention to provide a composition containing an organic nitric oxide donor compound which can be employed in the treatment of such anal disease(s).

It is also an object of the invention to provide a method of treating such anal disease(s) by contacting the affected area with an effective amount of nitric oxide delivered by release from an organic nitrate.

It is a further object of this invention to provide a composition containing an organic nitric oxide donor compound in combination with a corticosteroid and/or topical anesthetic which can be employed in the treatment of such anal disease(s).

It is a still further object hereof to provide a method of treating such anal disease(s) by contacting the affected area with an effective amount of nitric oxide delivered by release from an organic nitrate plus a corticosteroid and/or topical anesthetic.

To accomplish these and other related objects of the invention, the present invention provides, in one aspect, a pharmaceutical composition useful for treating anal disease without debilitating side effects comprising an organic nitric oxide donor in combination with a carrier, optionally with a corticosteroid and/or topical anesthetic. In one embodiment, if the organic nitric oxide donor is only nitroglycerin and the composition is a soft paraffin or petroleum based ointment then the nitroglycerin is present in an amount excluding 0.5 percent by weight, and optionally also excluding 0.2, 1 and/or 2 percent by weight. All weight percents expressed herein are based on the total weight of the composition. In another aspect, the invention is directed to a method for treating an anal disease comprising contacting an appropriate anal area with an effective amount of nitric oxide, preferably delivered by release from an organic nitric oxide donor. The method may also include optional application of a corticosteroid and/or topical anesthetic to the anal area. The present invention is useful in treatment of anal disease, especially anal fissure, anal ulcer, hemorrhoids and levator spasm. In many patients treatment can be obtained without debilitating side effects. Notably, and perhaps most significantly, anal pain can be rapidly and effectively controlled with the composition of the present invention.

DETAILED DESCRIPTION OF THE INVENTION

All references cited in the present specification are incorporated herein by reference.

In general herein, the term "anal" includes musculature and vasculature tissue of or proximate the anus and/or lower gut. The term "anal disease" means a disorder of the tissue which may include musculature and/or vasculature of or proximate the anus and/or lower gut. The term "organic nitric oxide donor" means an organic compound or mixture of compounds with at least one of such compound(s) which can release nitric oxide under physiological or anal disease treatment conditions.

The present invention concerns treatment directed at the underlying cause of anal diseases which include, for example, anal fissure, anal ulcer, hemorrhoids and/or levator spasm. In general, the cause of these diseases is believed to be an unidentified abnormality of the anal sphincter muscles.

The compositions useful for treatment according to the present invention can be in suitable topical, including suppository, form. An appropriate physiologically acceptable carrier is utilized to contain the organic nitric oxide donor, optionally with other agent(s) such as a corticosteroid and/or a topical anesthetic. The methods of treating anal diseases in accordance with the present invention can employ nitric oxide from any suitable source.

The invention may be employed in therapeutic medicine with human patients. Preferably, the organic nitric oxide donor includes at least one organic nitrate, which include esters of nitric acid and may be an acyclic or cyclic compound, such as represented by the following general formula:

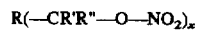

$$R(-CR'R''-O-NO_2)_x$$

wherein:

R is an organic or H (hydro) moiety or covalent bond, preferably a 2 to about 12 carbon hydrocarbon or oxygen-substituted hydrocarbon, especially one having 2 to 6 carbons and from 0 to 2 oxygen(s);

R' is an organic or hydro moiety or covalent bond, and preferably methyl; lower alkyl, to include ethyl, propyl, butyl, pentyl, and hexyl; methoxy; lower alkoxy; or hydro;

R" is an organic or hydro moiety or covalent bond, preferably methyl, lower alkyl, methoxy, lower alkoxy, or hydro, and especially hydro; and x is an integer from 1 to about 12, and preferably from 2 to 6.

For instance, the organic nitrate may be ethylene glycol dinitrate; isopropyl nitrate; glyceryl-1-mononitrate; glyceryl-1,2-dinitrate; glyceryl-1,3-dinitrate; nitroglycerin (GTN); butane-1,2,4-triol-trinitrate; erythrityl tetranitrate (ETN); pentaerythrityl tetranitrate (PETN); isosorbide mononitrate (ISMN), which may include isosorbide-2-mononitrate (IS2N) and/or isosorbide-5-mononitrate (IS5N); and/or isosorbide dinitrate (ISDN), and so forth and the like. An advantageous organic nitrate is GTN, and advantageous other organic nitrates include ISDN, ETN, PETN, etc., which may have been given regulatory approval for use in treatments in other fields of medicine on human subjects.

In general, the organic nitric oxide donor, to include the organic nitrate, is present in any amount which is effective in the practice of the treatment of anal disease. In typical practice of the invention the organic nitric oxide donor can be present in a concentration from about 0.01 to about 10 percent by weight. All weight percentages herein are based on the total weight of the composition. If GTN is the organic nitrate, preferred concentrations reside in the range of from about 0.01 to about 5 percent by weight. The following table lists some more particular general ranges for other organic nitrates in compositions of the invention:

| Compound | Approximate Weight Percents |
|---|---|
| ISDN | 0.01 to 7.5, to include 0.3 to 3 |
| ETN | 0.01 to 4, to include 0.1 to 1.5 |
| PETN | 0.01 to 4, to include 0.1 to 1.5 |

Optionally, a corticosteroid may be present in the compositions of the present invention. For instance, the corticosteroid may include hydrocortisone, i.e., 11-17-21-trihydroxypregn-4-ene-3,20-dione or cortisol, cortisol acetate, hydrocortisone phosphate, hydrocortisone 21-sodium succinate, hydrocortisone tebutate, corticosterone, corticosterone acetate, cortisone, cortisone acetate, cortisone 21B-cyclopentanepropionate, cortisone phosphate, triamcinolone hexacetonide, dexamethasone phosphate, desonide, betamethasone dipropionate, mometasone furate, and so forth and the like.

In general, the corticosteroid may be present in any amount which is effective in the practice of the treatment of anal disease. In typical practice of the invention, the corticosteroid can be present in a concentration from about 0.001 to about 10 percent by weight and preferably from about 0.1 to about 5 percent by weight. If cortisol is the corticosteroid, preferred concentrations reside in the range of from about 0.5 to about 2.5 percent by weight. If hydrocortisone is the corticosteroid, preferred concentrations reside in the range of from about 0.5 to about 5 percent by weight. If dexamethasone phosphate is the corticosteroid, preferred concentrations reside in the range of from about 0.005 to about 0.03 percent by weight.

Optionally, a topical anesthetic may be present in the composition of the invention. For instance, the topical anesthetic may include dibucaine, lidocaine, pramoxine, benzocaine, tetracaine, and so forth and the like. In general, the topical anesthetic may be present in any amount which is effective in the practice of the treatment of anal disease. In typical practice of the invention, the topical anesthetic can be present in a concentration from about 0.1 to about 5 percent by weight and preferably from about 0.5 to about 4 percent by weight based on the total weight of the composition. If dibucaine is the topical anesthetic, preferred concentrations reside in the range of from about 0.25 to about 2 percent by weight. If benzocaine is the topical anesthetic, preferred concentrations reside in the range of from about 10 to about 20 percent by weight. If tetracaine is the topical anesthetic, preferred concentrations reside in the range of from about 1 to about 2 percent by weight.

The corticosteroid and topical anesthetic may be employed together in the practice of the invention.

As those skilled in the art can appreciate, the composition of the invention may be formulated in any pharmaceutical state suitable for topical application, examples of which include liquid, aerosol, thickened liquid, emulsion, semisolid, powder, and a tablet or capsule, which may be lubricated for insertion into the anus. The method of the invention may employ any of such formulations as may be appropriate for treatment in particular cases. Advantageously, the composition can be formulated into highly convenient dosage forms with thickening agents to include thickened solutions or lotions, ointments to include creams and gels, and so forth.

Thickened solutions or lotions and ointments may be formed by incorporating with the active ingredients various gelling agents or other thickeners (viscosity increasers) which permit release of the active ingredients to the skin or tissue upon or following application. These forms are advantageously employed to lessen the runoff from the skin or tissue which may occur with more fluid (less viscous) formulations. Importantly, they also permit more sustained contact of the active ingredient(s) and any penetration enhancer with the treated surfaces, thus permitting an enhancement of the speed of delivery of the active ingredient(s) subcutaneously, and providing more accurate and controllable dosing. Accidental spilling and undesired contact with the composition can also be minimized with such types of formulations.

It can be advantageous to employ water-dispersible thickening agents, i.e., agents dispersible in water to form a homogeneous distribution or even solution, such as the polyethylene glycols and similar agents, as they are readily compatible with water or other diluents which may be formulated in the composition. Alternatively, an emulsion base may be employed to impart the desired thickening effect, together with the emollient effect of the lipoid phase of the emulsion base.

Water-soluble or water-dispersible thickening bases or substances may employ polyethylene glycols and the like of different viscosities depending upon the desired consistency and concentration of active ingredient(s) which may be incorporated into the composition. Other thickening agents which may be suitable for employment herein include but are not limited to water-dispersible gums, carboxyvinyl polymers, methyl cellulose, sodium carboxymethyl cellulose, and alginates.

Lotions and ointments incorporating emulsion bases may contain the usual ingredients to provide the base, including fatty alcohols such as acetyl alcohol, an emulsifier such as, for example, lauryl sulfate, and water. Also, the remainder of a topical preparation may contain one or more conventional ointment components such as, for example, white petrolatum, lanolin, distilled water, and mineral oil in conventional amounts. The remainder of a suppository may contain conventional amounts of known suppository components such as, for example, zinc oxide and/or cocoa butter.

Pourable pharmaceutical dosages may be provided and dispensed in graduated containers, or in containers which contain a given volume, say, for example, 5 or 10 cc, and so forth. Containers with greater volumes, say, for example, of 20 cc and greater, can provide convenient multiple dosage forms. Containers containing a typical single dose, for example, from about 0.5 g to about 10 g of active ingredient (s), can provide convenient dosage forms. Squeeze tubes for lotions and ointments and cotton stick applicators may be employed for topical application of the composition for liquids ranging from those of water-like viscosity to the more viscous formulations of thickened compositions and for powders and the like.

Dusts may be employed. An inert ingredient such as, for example, starch and/or talc may be employed to dilute the active ingredient(s) in powder form.

The composition of the invention, and the ingredient(s) in a method, may also be administered by dusting, spraying or misting such as from shakers, dusting devices, misting devices and aerosol bottles. Containers of the composition may be charged with any suitable amount and concentration of ingredient(s). As an illustration, a container may be charged with a fluid formulation containing at least about 10 percent by weight of a combination of active ingredients, along with an aqueous diluent, optionally with thickening agent(s), physiological salt(s), and so forth. Liquid compositions, for example, may be administered as low viscosity substances to semisolid gels or mousses, depending on any amount of gelling agent(s) and/or surfactant(s) included therein. Such compositions can be sufficiently fluid to permit their dispensing by spray or mist from the container and also can meet criteria for penetrability.

In treatment according to the invention, an amount of active ingredient(s) or composition of the invention is contacted with or applied to the affected anal area or proximate thereto such that an effective amount of nitric oxide, preferably delivered by release from an organic nitric oxide donor, is administered. The amount of active ingredient(s) or composition which is employed should be effective for the amelioration, control and/or healing of the anal disease and the prompt and dramatic control or relief of pain resulting from or associated with the disease. For example, an ointment composition of the invention can be applied topically at each application to the external anus and to the distal anal canal with the finger or an applicator. As an illustrative alternative, the medication can be delivered intra-rectally as a suppository. The medication can be applied in this fashion, for example, three or more times daily in the case of the ointment or once or more times daily in the case of the suppository.

Employment of the optional corticosteroid and/or topical anesthetic in the practice of the invention can provide decidedly advantageous results. In cases where treatment with an organic nitrate alone as active treating agent fails to provide relief from pain and/or healing, most notably, the employment of the corticosteroid and/or topical anesthetic in combination with the organic nitrate often can provide significant if not complete relief from pain and provide for significant if not total healing as well.

Pain relief from the invention is rapid and often dramatic.

The following examples further illustrate the present invention. All parts and percentages (percent or %) therein are by weight, unless otherwise specified.

EXAMPLE 1

An ointment was prepared by admixing 12.5 g of 2 percent nitroglycerin in white petrolatum, lanolin, and distilled water (nitroglycerin ointment, USP 2%; E. Fougera & Co., Melville, N.Y.) with 37.5 g white petrolatum, USP (VASELINE; Chesebrough-Ponds USA Co., Greenwich, Conn.) in a laboratory mixing vessel at room temperature. The resulting mixture was 50 g of a 0.5 percent nitroglycerin ointment.

EXAMPLE 2

An ointment of 12.5 g of 2 percent nitroglycerin in white petrolatum, lanolin, and distilled water (nitroglycerin ointment, USP 2%; E. Fougera & Co., Melville, N.Y.) was admixed with 20 g of 2.5 percent hydrocortisone in white petrolatum and light mineral oil (hydrocortisone ointment, USP 2.5%; Clay-Park Labs, Inc., Bronx, N.Y.) and with 17.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin and 1 percent hydrocortisone ointment.

EXAMPLE 3

An ointment of 12.5 g of 2 percent nitroglycerin in white petrolatum, lanolin, and distilled water (nitroglycerin ointment, USP 2%; E. Fougera & Co., Melville, N.Y.) was admixed with 25 g of 1 percent dibucaine, USP, in white petrolatum, light mineral oil, acetone sodium bisulfite, lanolin, and purified water (NUPERCAINAL; Ciba Consumer Pharmaceuticals, Edison, N.J.) and with 12.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin and 0.5 percent dibucaine ointment.

EXAMPLE 4

An ointment of 2.5 g of 2 percent nitroglycerin in white petrolatum, lanolin, and distilled water (nitroglycerin ointment, USP 2%; E. Fougera & Co., Melville, N.Y.) was admixed with 20 g of 2.5 percent hydrocortisone in white petrolatum and light mineral oil (hydrocortisone ointment, USP 2.5%; Clay-Park Labs, Inc., Bronx, N.Y.) and with 25 g of 1 percent dibucaine, USP, in white petrolatum, light mineral oil, acetone sodium bisulfite, lanolin, and purified water (NUPERCAINAL; Ciba Consumer Pharmaceuticals, Edison, N.J.) and with 2.5 g of white petrolatum, USP (VASELINE; Chesebrough-Ponds USA Co., Greenwich, Conn.) in a laboratory mixing vessel at room temperature. The resulting mixture was 50 g of a 0.5 percent nitroglycerin, 1 percent hydrocortisone, and 0.5 percent dibucaine ointment.

EXAMPLE 5

A 29-year old female had a 7-day history of anal pain and bleeding with bowel movements. Physical exam showed posterior midline anal fissure. The patient rated her pretreatment pain 7/10. The patient applied approximately 500 mg of the ointment as prepared in Example 1, three times daily and after bowel movements. The patient reported that her pain was gone following initial application. After two weeks of treatment, the fissure had healed completely.

EXAMPLE 6

A 40-year old female had a 3-month history of anal pain and bleeding with bowel movements. Physical examination showed a superficial posterior midline anal fissure. The patient rated her pre-treatment pain 7/10. The patient applied approximately 500 mg of the ointment as prepared in Example 1, three times daily and after bowel movements. After one week of treatment, the patient noted persistent bleeding, but her pain was rated 2/10. After three weeks of treatment, the fissure was healed, and the pain was gone.

EXAMPLE 7

A 36-year old man had a 2-year history of anal pain and bleeding with bowel movements. Examination showed a posterior midline anal ulcer. Pre-treatment pain was rated 9/10. The patient was treated with hydrocortisone/ pramoxine cream (ANALPRAM-HC, 2.5%; Ferndale Laboratories, Inc., Ferndale, Mich.) three times daily and following bowel movements. After one week of treatment, the patient rated his pain 6/10, and the physical condition was essentially unchanged. The patient was then treated with approximately 500 mg of the ointment as prepared in Example 2, three times daily and after bowel movements. He reported "immediate" relief of pain with each application. After one week of such therapy, the ulcer was smaller, but not yet completely healed.

EXAMPLE 8

A 23-year old female had a 1-month history of anal pain and bleeding with bowel movements. Examination showed a superficial posterior midline anal fissure. She had previously failed a course of hydrocortisone therapy. Pre-treatment pain was rated 9/10. The patient was treated with approximately 500 mg of the preparation of Example 1, three times daily and after bowel movements. After one week of treatment, the fissure was still present, and pain was rated 8/10. The patient was then treated with approximately 500 mg of the preparation of Example 2, three times daily and after bowel movements. Following one week of therapy with the ointment as of Example 2, the patient reported no pain and no bleeding. Subsequent examination showed that the fissure had healed.

EXAMPLE 9

A 27-year old female had a 3-day history of anal pain and bleeding with bowel movements. Physical examination showed a superficial anterior midline anal fissure. Pre-treatment pain was rated 4/10. The patient was treated with the ointment as of Example 2, approximately 500 mg three times daily and after bowel movements. Following one week of therapy, the patient reported that her pain had diminished, and it was rated 2/10. Examination showed improvement. After another fifteen days of therapy, the patient was pain free, and the fissure had healed.

EXAMPLE 10

A 27-year old man presented with a 5-day history of anal pain. Physical examination revealed a 1-cm thrombosed external hemorrhoid in the left anterolateral anal quadrant. The patient was treated with the ointment as of Example 3, approximately 500 mg three times daily and after bowel movements. He reported a significant reduction in anal pain and throbbing three days later.

EXAMPLE 11

A 57-year old man was referred for treatment of documented levator spasm which developed following lower spinal surgery two years before. The patient was treated with the ointment as of Example 1, approximately 500 mg intra-anally three times daily and after bowel movements. He reported improvement of the anorectal spasm within one day. Treatment was then switched to the preparation of Example 3, approximately 500 mg intra-anally three times daily and after bowel movements. Pain relief was not as great, and so, treatment with the preparation as of Example 1 was restarted.

EXAMPLE 12—GROUP STUDIES

Methods

TEH Group: Five patients (three women and two men) were recruited to participate in a trial of topical nitroglycerin treatment for acutely thrombosed external hemorrhoids (TEH). Their ages ranged from 23 to 51 years old. The duration of their symptoms ranged from 2 to 4 days. Anorectal examination of all of these patients revealed TEH in one anal quadrant (three patients) and in two anal quadrants (two patients). None of these patients had evidence of internal hemorrhoid thrombosis, fissure, abscess, or fistula. All of these patients had used one or more topical preparations (ANUSOL or ANUSOL-HC, Parke-Davis, Morris Plains, N.J.; PREPARATION H, Whitehall Laboratories, Madison, N.J.; PROCTOCREAM-HC, Reed & Carnrick, Jersey City, N.J.) without symptomatic relief.

Fissure Group: Fifteen patients (ten women and five men) were recruited to participate in a trial of topical nitroglycerin treatment for anal fissure or ulcer. Their ages ranged from 23 to 61 years old. The duration of their symptoms ranged from 2 days to 2 years. Three patients had posterior midline anal ulcers; eleven had acute, posterior midline fissures; one had an acute, anterior midline anal fissure. Two patients had a history of Crohn's ileitis. None of these patients had a history of recent anal surgery.

After obtaining informed consent from each participant, a program of therapy was begun. Treatment included psyllium seed (12 g daily) and sitz baths as needed. Approximately 500 to 1000 mg of 0.5 percent nitroglycerin ointment as in Example 1 was applied with the finger to the external anus and distal anal canal four or more times daily and after bowel movements. All patients were interviewed and examined one week after initiating the therapy. Patients of the fissure group were re-examined three weeks after initiating therapy, and every one week or two weeks thereafter until either the fissure had healed or eight weeks of the therapy had passed.

Results

TEH Group: All patients reported total or near total relief of anal pain within 2 to 3 minutes of nitroglycerin application. The nitroglycerin was especially useful in relieving the pain which typically occurred following defecation. Each application of the nitroglycerin ointment relieved anal pain from 4 to 6 hours in all patients. All patients reported the need for fewer sitz baths. The nitroglycerin ointment was used for an average of three days (range two to six days). Resolution of the thrombus appeared to follow the usual time course. Side effects were limited to transient headache in two patients (40 percent of the group population).

Fissure Group: All patients reported dramatic relief of anal pain within 3 to 4 minutes of application of the nitroglycerin ointment, and the effect of pain relief was sustained from 2 to 6 hours. Most patients reported that the nitroglycerin ointment was especially useful in relieving the pain that occurred following defecation. Fourteen patients applied the ointment every four to six hours while awake. One patient required application every two to three hours to achieve satisfactory pain control. Of the twelve with superficial anal fissures, ten (83 percent of this set) were healed within two weeks, and this set included the two patients with Crohn's disease. Two patients who had discontinued treatment after complete healing at two weeks had recurrences of their fissures. Both responded to another two weeks of therapy with no further recurrence of symptoms. The remaining two patients with anal fissures healed after four weeks of continuous treatment. One patient with a posterior anal ulcer was improved but not completely healed after two weeks of therapy. She requested sphincterotomy which resulted in complete healing within another month. Two patients with posterior anal ulcers were improved but not completely healed after two months of therapy, and sphincterotomy was refused in both cases. Side effects were limited to mild, transient headaches in five patients (33 percent of the group population).

The twenty patients in this study experienced dramatic pain relief after the first dose of the topically applied nitroglycerin ointment, and healing was significant. The nitroglycerin ointment topically applied to the anal and rectal area was well tolerated by most patients in this study. Seven of the twenty human subjects (35 percent of the groups population) experienced headaches after topical application of the nitroglycerin ointment. The headaches were generally self-limited and abated after about fifteen minutes.

EXAMPLE 13

An ointment is prepared by admixing 8.75 g of 2 percent nitroglycerin in white petrolatum, lanolin, and distilled water (nitroglycerin ointment, USP 2%; E. Fougera & Co., Melville, N.Y.) with 41.25 g white petrolatum, USP (VASELINE; Chesebrough-Ponds USA Co., Greenwich, Conn.) in a laboratory mixing vessel at room temperature. The resulting mixture is 50 g of a 0.35 percent nitroglycerin ointment.

The ointment is effective in the treatment of anal disease when applied topically to or proximate the affected area. Therewith, pain relief and healing are significant, and side effects such as headache are few and/or mild. The ointment can be employed with humans.

Conclusion

From the foregoing, it will be seen that this invention is one well adapted to attain all the ends and objects hereinabove set forth.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

What is claimed is:

1. A method for treating an anal disease comprising contacting an appropriate anal area with a composition comprising an effective amount of nitroglycerin.

2. The method as set forth in claim 1, wherein the nitroglycerin is present in the composition in an amount of from about 0.01 to about 5% by weight.

3. A method for treating an anal disease comprising contacting an appropriate anal area with an effective mount of nitric oxide delivered by release from a composition comprising an organic nitric oxide donor, wherein at least one agent selected from the group consisting of a corticosteroid and a topical anesthetic is employed in conjunction with the nitric oxide donor.

4. The method as set forth in claim 3, wherein the organic nitric oxide donor is present in the composition in an amount from about 0.01 to about 5 percent by weight.

5. The method of claim 3, wherein at least one agent selected from the group consisting of a corticosteroid and a topical anesthetic is employed in conjunction with the nitric oxide donor.

6. The method of claim 5, wherein the corticosteroid is hydrocortisone, and the topical anesthetic is dibucaine.

7. A method for treating an anal disease and controlling pain associated therewith comprising contacting an appropriate anal area with an effective amount of nitric oxide.

8. The method as set forth in claim 7, wherein the nitric oxide is delivered by release from a composition comprising an organic nitric oxide donor.

9. The method as set forth in claim 8, wherein the organic nitric oxide donor is present in the composition in an amount of from about 0.01 to about 10% by weight.

10. The method as set forth in claim 9, wherein the organic nitric oxide donor is an organic nitrate represented by the following general formula:

$$R(-CR'R''-O-NO_2)_x$$

wherein:

R, R' and R'' are, independently at each occurrence, organic or hydro moiety or covalent bond, and x is an integer from 1 to about 12.

11. The method as set forth in claim 10, wherein

R is a 2 to about 12 carbon hydrocarbon or oxygen-substituted hydrocarbon;

R' is of 2 to 6 carbons and from 0 to 2 oxygen(s), a hydro moiety or a covalent bond;

R'' is a hydro moiety; and x is from 2 to 6.

12. The method as set forth in claim 7, wherein the nitric oxide is delivered by release from a composition comprising an effective amount of one or more of ethylene glycol dinitrate, isopropyl nitrate, glyceryl-1-mononitrate, glyceryl-1,2-dinitrate, glyceryl-1,3-dinitrate, nitroglycerin, butane-1,2,4-triol-trinitrate, erythrityl tetranitrate, pentaerythrityl tetranitrate, isosorbide mononitrate, and isosorbide dinitrate.

13. The method as set forth in claim 7, wherein the nitric oxide is delivered by release from a composition comprising an effective amount of nitroglycerin.

14. The method as set forth in claim 7, wherein the nitric oxide is delivered by release from a composition comprising from about 0.01 to about 5% by weight nitroglycerin.

15. The method as set forth in claim 7, wherein the nitric oxide is delivered by release from a composition comprising an effective amount of isosorbide dinitrate.

16. The method as set forth in claim 7, wherein the nitric oxide is delivered by release from a composition comprising from about 0.01 to about 7.5% isosorbide dinitrate.

17. The method as set forth in claim 7, wherein the nitric oxide is delivered by release from a composition comprising an effective amount of erythrityl tetranitrate.

18. The method as set forth in claim 7, wherein the nitric oxide is delivered by release from a composition comprising from about 0.01 to about 4% by weight erythrityl tetranitrate.

19. The method as set forth in claim 7, wherein the nitric oxide is delivered by release from a composition comprising an effective amount of pentaerythrityl tetranitrate.

20. The method as set forth in claim 7, wherein the nitric oxide is delivered by release from a composition comprising from about 0.01 to about 4% by weight pentaerythrityl tetranitrate.

21. A method for treating an anal fissure or anal ulcer comprising contacting an appropriate anal area with an effective amount of nitric oxide.

22. The method as set forth in claim 21, wherein the nitric oxide is delivered by release from a composition comprising an organic nitric oxide donor.

23. The method as set forth in claim 22, wherein the organic nitric oxide donor is present in the composition in an amount of from about 0.01 to about 10% by weight.

24. The method as set forth in claim 23, wherein the organic nitric oxide donor is an organic nitrate represented by the following general formula:

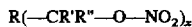

wherein:
R, R' and R" are, independently at each occurrence, organic or hydro moiety or covalent bond, and
x is an integer from 1 to about 12.

25. The method as set forth in claim 24, wherein
R is a 2 to about 12 carbon hydrocarbon or oxygen-substituted hydrocarbon;
R' is of 2 to 6 carbons and from 0 to 2 oxygen(s), a hydro moiety or a covalent bond;
R" is a hydro moiety; and
x is from 2 to 6.

26. The method as set forth in claim 21, wherein the nitric oxide is delivered by release from a composition comprising an effective mount of one or more of ethylene glycol dinitrate, isopropyl nitrate, glyceryl-1-mononitrate, glyceryl-1,2-dinitrate, glyceryl-1,3-dinitrate, nitroglycerin, butane-1,2,4-triol-trinitrate, erythrityl tetranitrate, pentaerythrityl tetranitrate, isosorbide mononitrate, and isosorbide dinitrate.

27. The method as set forth in claim 21, wherein the nitric oxide is delivered by release from a composition comprising an effective amount of nitroglycerin.

28. The method as set forth in claim 21, wherein the nitric oxide is delivered by release from a composition comprising from about 0.01 to about 5% by weight nitroglycerin.

29. The method as set forth in claim 21, wherein the nitric oxide is delivered by release from a composition comprising an effective amount of isosorbide dinitrate.

30. The method as set forth in claim 21, wherein the nitric oxide is delivered by release from a composition comprising from about 0.01 to about 7.5% isosorbide dinitrate.

31. The method as set forth in claim 21, wherein the nitric oxide is delivered by release from a composition comprising an effective amount of erythrityl tetranitrate.

32. The method as set forth in claim 21, wherein the nitric oxide is delivered by release from a composition comprising from about 0.01 to about 4% by weight erythrityl tetranitrate.

33. The method as Set forth in claim 21, wherein the nitric oxide is delivered by release from a composition comprising an effective amount of pentaerythrityl tetranitrate.

34. The method as set forth in claim 21, wherein the nitric oxide is delivered by release from a composition comprising from about 0.01 to about 4% by weight pentaerythrityl tetranitrate.

35. A method for treating hemorrhoid disease comprising contacting an appropriate anal area with an effective amount of nitric oxide.

36. The method as set forth in claim 35, wherein the nitric oxide is delivered by release from a composition comprising an organic nitric oxide donor.

37. The method as set forth in claim 36, wherein the organic nitric oxide donor is present in the composition in an amount of from about 0.01 to about 10% by weight.

38. The method as set forth in claim 37, wherein the organic nitric oxide donor is an organic nitrate represented by the following general formula:

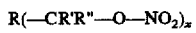

wherein:
R, R' and R" are, independently at each occurrence, organic or hydro moiety or covalent bond, and
x is an integer from 1 to about 12.

39. The method as set forth in claim 38, wherein
R is a 2 to about 12 carbon hydrocarbon or oxygen-substituted hydrocarbon;
R' is of 2 to 6 carbons and from 0 to 2 oxygen(s), a hydro moiety or a covalent bond;
R" is a hydro moiety; and
x is from 2 to 6.

40. The method as set forth in claim 35, wherein the nitric oxide is delivered by release from a composition comprising an effective amount of one or more of ethylene glycol dinitrate, isopropyl nitrate, glyceryl-1-mononitrate, glyceryl-1,2-dinitrate, glyceryl-1,3-dinitrate, nitroglycerin, butane-1,2,4-triol-trinitrate, erythrityl tetranitrate, pentaerythrityl tetranitrate, isosorbide mononitrate, and isosorbide dinitrate.

41. The method as set forth in claim 35, wherein the nitric oxide is delivered by release from a composition comprising an effective mount of nitroglycerin.

42. The method as set forth in claim 35, wherein the nitric oxide is delivered by release from a composition comprising from about 0.01 to about 5% by weight nitroglycerin.

43. The method as set forth in claim 35, wherein the nitric oxide is delivered by release from a composition comprising an effective amount of isosorbide dinitrate.

44. The method as set forth in claim 35, wherein the nitric oxide is delivered by release from a composition comprising from about 0.01 to about 7.5% isosorbide dinitrate.

45. The method as set forth in claim 35, wherein the nitric oxide is delivered by release from a composition comprising an effective amount of erythrityl tetranitrate.

46. The method as set forth in claim 35, wherein the nitric oxide is delivered by release from a composition comprising from about 0.01 to about 4% by weight erythrityl tetranitrate.

47. The method as set forth in claim 35, wherein the nitric oxide is delivered by release from a composition comprising an effective mount of pentaerythrityl tetranitrate.

48. The method as set forth in claim 35, wherein the nitric oxide is delivered by release from a composition comprising from about 0.01 to about 4% by weight pentaerythrityl tetranitrate.

49. A method for treating levator spasm comprising contacting an appropriate anal area with an effective amount of nitric oxide.

50. The method as set forth in claim 49, wherein the nitric oxide is delivered by release from a composition comprising an organic nitric oxide donor.

51. The method as set forth in claim 50, wherein the organic nitric oxide donor is present in the composition in an amount of from about 0.01 to about 10% by weight.

52. The method as set forth in claim 51, wherein the organic nitric oxide donor is an organic nitrate represented by the following general formula:

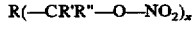

wherein:
R, R' and R" are, independently at each occurrence, organic or hydro moiety or covalent bond, and x is an integer from 1 to about 12.

53. The method as set forth in claim 52, wherein

R is a 2 to about 12 carbon hydrocarbon or oxygen-substituted hydrocarbon;

R' is of 2 to 6 carbons and from 0 to 2 oxygen(s), a hydro moiety or a covalent bond;

R" is a hydro moiety; and x is from 2 to 6.

54. The method as set forth in claim 49, wherein the nitric oxide is delivered by release from a composition comprising an effective amount of one or more of ethylene glycol dinitrate, isopropyl nitrate, glyceryl-1-mononitrate, glyceryl-1,2-dinitrate, glyceryl-1,3-dinitrate, nitroglycerin, butane-1,2,4-triol-trinitrate, erythrityl tetranitrate, pentaerythrityl tetranitrate, isosorbide mononitrate, and isosorbide dinitrate.

55. The method as set forth in claim 49, wherein the nitric oxide is delivered by release from a composition comprising an effective amount of nitroglycerin.

56. The method as set forth in claim 49, wherein the nitric oxide is delivered by release from a composition comprising from about 0.01 to about 5% by weight nitroglycerin.

57. The method as set forth in claim 49, wherein the nitric oxide is delivered by release from a composition comprising an effective amount of isosorbide dinitrate.

58. The method as set forth in claim 49, wherein the nitric oxide is delivered by release from a composition comprising from about 0.01 to about 7.5% isosorbide dinitrate.

59. The method as set forth in claim 49, wherein the nitric oxide is delivered by release from a composition comprising an effective amount of erythrityl tetranitrate.

60. The method as set forth in claim 49, wherein the nitric oxide is delivered by release from a composition comprising from about 0.01 to about 4% by weight erythrityl tetranitrate.

61. The method as set forth in claim 49, wherein the nitric oxide is delivered by release from a composition comprising an effective amount of pentaerythrityl tetranitrate.

62. The method as set forth in claim 49, wherein the nitric oxide is delivered by release from a composition comprising from about 0.01 to about 4% by weight pentaerythrityl tetranitrate.

* * * * *